United States Patent [19]
Schroder et al.

[11] Patent Number: 6,153,775
[45] Date of Patent: Nov. 28, 2000

[54] POLYDENTATE IMINES AND THEIR METAL COMPLEXES

[75] Inventors: Martin Schroder, Nottingham; Daniel Martin John Doble, Solihull, both of United Kingdom

[73] Assignee: NYCOMED Amersham PLC., Little Chalfont, United Kingdom

[21] Appl. No.: 09/380,698

[22] PCT Filed: Mar. 6, 1998

[86] PCT No.: PCT/GB98/00678

§ 371 Date: Dec. 27, 1999

§ 102(e) Date: Dec. 27, 1999

[87] PCT Pub. No.: WO98/39288

PCT Pub. Date: Sep. 11, 1998

[30] Foreign Application Priority Data

Mar. 7, 1997 [EP] European Pat. Off. ............. 97301548

[51] Int. Cl.[7] .............................. C07F 5/00; C07C 229/00
[52] U.S. Cl. .................................. 556/1; 534/15; 534/16; 562/14; 562/17; 562/553; 562/565; 562/571

[58] Field of Search ...................................... 562/565, 553, 562/571, 14, 17; 556/1; 534/15, 16

[56] References Cited

U.S. PATENT DOCUMENTS 5,071,965 12/1991 Dunn et al. .............................. 534/14
5,405,601 4/1995 Dunn et al. .................................. 424/9

FOREIGN PATENT DOCUMENTS 0491594 6/1992 European Pat. Off. .
4406465 A1 8/1995 Germany .

OTHER PUBLICATIONS

Orvig et al., Inorganic Chemistry, vol. 27, No. 22, pp. 3929–3934, 1988.

*Primary Examiner*—Porfirio Nazario-Gonzalez
*Attorney, Agent, or Firm*—Marshall, O'Toole, Gerstein, Murray & Borun

[57] ABSTRACT

Tripodal chelating agents incorporating imine C=N bonds are disclosed for the formation of lanthanide and other metal complexes which are relatively stable in the presence of water at neutral pH.

11 Claims, 3 Drawing Sheets

POLYDENTATE IMINES AND THEIR METAL COMPLEXES

The present invention relates to novel ligands for complexing metal ions, especially lanthanide metals such as gadolinium, samarium or ytterbium, as well as metals known to exhibit similar chemistry such as yttrium, plus the main group metals indium and gallium.

α-Imine carboxylic acids which comprise an imine and a carboxylate donor of formula:

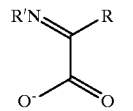

R = H, Me, Et
R' = Me, iPr, Ph, CH$_2$Ph are known to function as bidentate ligands for metal ions forming 5-membered chelate rings at a single metal centre, i.e. mononuclear metal complexes. Metal complexes have been prepared with the transition metals molybdenum, iron, ruthenium, cobalt, rhodium, iridium, copper, palladium and platinum, plus the main group metals aluminium and zinc [M. Yamaguchi et al, Inorg.Chem., 35, 143(1996)].

Tetradentate N$_2$O$_2$ diiminedicarboxylic acid analogues have been prepared and shown to bridge two transition metal centres forming binuclear metal complexes of cobalt or iridium [K. Severin et al., Z.Naturforsch.B, 50, 265,(1995)] as opposed to chelating a single metal centre:

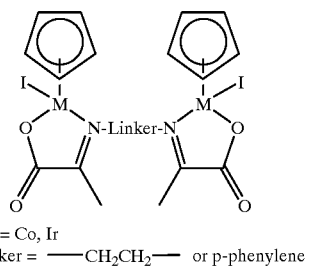

M = Co, Ir
linker = —CH$_2$CH$_2$— or p-phenylene

Polydentate Schiff base ligands and their complexation with lanthanide metals are known. Thus Orvig et al [Inorg.Chem.,27, 3929(1988)] prepared potentially heptadentate N$_4$O$_3$ ligands and studied their metal complexation with lanthanide metals:

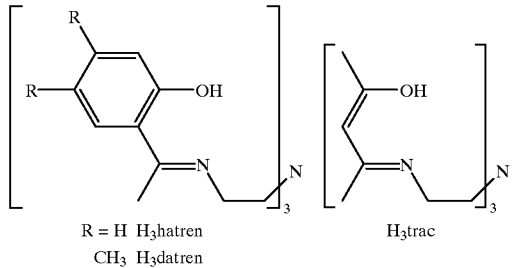

R = H H$_3$hatren
CH$_3$ H$_3$datren

H$_3$trac

The lanthanide (Ln) complexes of H$_3$hatren, H$_3$datren and H$_3$trac of formula Ln(ligand) in which the ligand functions as an N$_4$O$_3$ heptadentate donor were found to be unstable, undergoing facile decomposition via hydrolysis or solvent displacement of coordinated donor atoms. Orvig et al later reported [(J.Am.Chem.Soc., 113, 2528(1991)] the X-ray crystal structure of the neutral ytterbium complex Yb(trac). This heptadentate complex could only be unambiguously characterised under rigorously anhydrous conditions. The rapid hydrolysis of these complexes in the presence of water led Orvig et al to conclude that this class of lanthanide complexes was too unstable to be useful as MRI contrast agents. Subsequent work focused on developing analogous ligand systems with saturated CH—NH bonds in place of the C=N imine bond, since the ease of solvolysis was ascribed to the presence of the imine bond.

The possibility of a radiometal ($^{99m}$Tc) coordinated imine undergoing hydrolytic cleavage both in vitro and in vivo has previously been noted [G. F. Morgan et al, J.Nucl.Med., 32, 500(1991)]. The ligand studied was the tetradentate N$_3$O ligand MRP20:

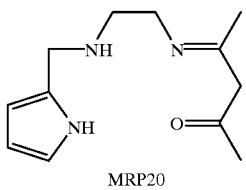

MRP20

It has now been found that a novel class of tripodal chelating agents incorporating imine C=N bonds form lanthanide and other metal complexes which are relatively stable in the presence of water at neutral pH.

The present invention provides, in a first aspect, a ligand of formula:

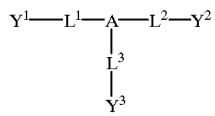

where:
A is N, CR$^1$, P, P=O, cis,cis,cis-1,3,5-trisubstituted-cyclohexane or an N,N',N''-trisubstituted-triaza 9 to 14 membered macrocyclic ring;

L$^1$, L$^2$, L$^3$ are linker groups which are independently chosen from C$_{1-4}$ alkylene, C$_{4-6}$ cycloalkylene or C$_{4-6}$ o-arylene;

Y$^1$, Y$^2$, Y$^3$ are independently chosen from —NH$_2$, —B(=O)OZ, —N=CR—B(=O)OZ, —NR—CR$_2$—B(=O)OZ, —N[CR$_2$—B(=O)Q]$_2$ and —O—CR$_2$—B(=O)OZ where B is C or PR$^2$, each Q is independently —OZ or —NR$_2$ and Z is H or a counter-ion;

each R and R$^1$ group is independently chosen from H, C$_{1-5}$ alkyl, C$_{1-5}$ alkoxyalkyl, C$_{1-5}$ hydroxyalkyl, C$_{1-5}$ aminoalkyl, C$_{5-10}$ aryl or C$_{1-6}$ fluoroalkyl;

R$^2$ is OH, C$_{1-6}$ alkyl, C$_{1-6}$ alkoxyalkyl, C$_{1-6}$ fluoroalkyl, C$_{1-10}$ alkoxy or C$_{5-10}$ aryl;

with the proviso that at least one of Y$^1$, Y$^2$ and Y$^3$ is —N=CR—B(=O)OZ.

A is preferably N or CR$^1$, L$^1$, L$^2$ and L$^3$ are preferably C$_{1-3}$ alkylene, most preferably C$_{1-2}$ alkylene. The N,N',N''-trisubstituted-triaza 9 to 14 membered macrocyclic ring has preferably 9–12 members, and is most preferably 1,4,7-trisubstituted-1,4,7-triazacyclononane. For lanthanide metals and yttrium , Y$^1$, Y$^2$ and Y$^3$ are preferably chosen from —O—CR$_2$—B(=O)OZ, —N[CR$_2$—B(=O)Q]$_2$ and —N=CR—B(=O)OZ. Most preferred ligands are those where A is N, L$^1$, L$^2$ and L$^3$ are all —CH$_2$CH$_2$— and B is C. Preferably Z is H or an alkali metal or a C$_{1-10}$ tetraalkyl or tetraaryl ammonium or phosphonium ion.

The ligands of the present invention can be used to prepare metal complexes of lanthanide metals or suitably chosen metals of similar chemistry such as yttrium, or other suitably chosen main group metals such as indium and gallium. When the metal ion is paramagnetic or radioactive the metal complex may be useful for in vivo diagnostic imaging, especially of the human body. Thus paramagnetic metal complexes are useful as MRI contrast agents, and radioactive metal complexes are useful as radiopharmaceuticals for in vivo imaging or radiotherapy. The metal complexes may also be useful for in vivo diagnostic imaging as X-ray contrast agents using the fact that the metal atom is opaque to X-rays, i.e. radiopaque.

When A is N and each of $L^1$, $L^2$ and $L^3$ is ethylene and each of $Y^1$, $Y^2$ and $Y^3$ is —N=CR—C(=O)OZ, the metal complex may have the formula (1):

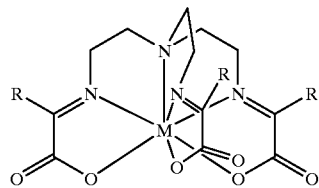

The metal complexes of the present invention may contain one or more metal ions which may be the same or different. Polynuclear complexes may have advantageous properties, e.g. certain metal clusters have superparamagnetic properties and are hence particularly useful as MRI contrast agents. Metal complexes of the present invention may have 1 to 6 metal atoms. For MRI or X-ray contrast applications, the complexes preferably have 1 to 4 metal atoms. For radiopharmaceutical applications the complexes preferably have a single metal atom, i.e. are mononuclear. When the metal of the metal complex is a radiometal, it can be either a positron emitter (such as $^{68}$Ga, $^{132}$La, $^{150}$Tb, $^{155}$Dy or $^{161}$Er) or a γ-emitter such as $^{111}$In, $^{113m}$In or $^{67}$Ga. Suitable metal ions for use in MRI are the paramagnetic lanthanide metal ions gadolinium(III), samarium(III), erbium(III), terbium(III), ytterbium(III), dysprosium(III), holmium(III), neodymium(III) and praseodymium(III). Preferred paramagnetic metal ions are gadolinium(III) and samarium(III). Most preferred radiometals for diagnostic imaging are γ-emitters, especially $^{111}$In, $^{113m}$In and $^{67}$Ga. Metal complexes of certain alpha-emitter or beta-emitter radionuclides may be useful as radiopharmaceuticals for the radiotherapy of various diseases such as cancer. The beta-emitter may be suitably chosen from: $^{90}$Y, $^{114}$In, $^{115m}$In, $^{140}$La, $^{149}$Pm, 153Sm, $^{159}$Gd, $^{161}$Tb, $^{165}$Dy, $^{166}$Ho, $^{169}$Er, $^{175}$Yb and 177Lu. Preferred beta-emitter radiometals for radiotherapeutic applications are: $^{90}$Y, $^{153}$Sm, 159Gd, $^{165}$Dy, $^{169}$Er, $^{166}$Ho, $^{175}$Yb and $^{177}$Lu. Most preferred beta-emitter radiometals for radiotherapeutic applications are: $^{90}$Y, $^{153}$Sm and $^{166}$Ho. Suitable metals for X-ray contrast imaging include gadolinium, dysprosium, holmium and praseodymium. The ligands of the present invention may also be used in the extraction of metals from their ores. The avidity of the ligands for lanthanide and related metals may provide the basis for selective complexation. The metal or metals to be extracted could be complexed under neutral or alkaline conditions, separated and/or purified as necessary, and then the ligand removed under acid conditions using the acid-sensitivity of the metal complexes (see below).

The ligands of the present invention may be prepared by condensation of an α-ketoacid of formula R(C=O)B(=O)OZ with the appropriate mono-, di- or tri-primary amine of formula $A(L^1Y^1)(L^2Y^2)(L^3Y^3)$ in which at least one of $Y^1$, $Y^2$ and $Y^3$ is $NH_2$ in an organic solvent. The water generated may optionally be removed in situ by for example, azeotropic distillation in benzene, or the addition of a drying agent. The isolated ligand can then be reacted in a second step with the metal ion of interest to give the desired metal complex. Alternatively, it may be convenient to carry out the above condensation reaction in the presence of the metal ion of interest, in which case the metal complex forms directly in situ in a one step process (a so-called metal template synthesis). If the metal complex is prepared in this way the free ligand can be obtained by displacement of the ligand from the metal using a competing ligand which is much more avid for the metal in question (i.e. transchelation). The displacing ligand may be suitably chosen from a crown ether, a polydentate macrocyclic ligand such as DOTA or cyanide, sulphide (via treatment with hydrogen sulphide) or other suitable displacing ligands known to those skilled in the art.

Depending upon the charge on the metal ion and the degree of ionisation of the ligand, the metal complexes of the present invention may be either charged or neutral (i.e. non-ionic). Neutral metal complexes are preferred since the absence of electrical charge on the complex means that, if the complex does not carry overly hydrophilic substituent (s), it will be sufficiently lipophilic to cross lipid membranes such as cell membranes or the blood-brain barrier. Such complexes are therefore particularly useful for brain or spinal cord imaging. Neutral, lipophilic metal complexes are also capable of crossing cell membranes and hence may be useful for a range of other applications including blood cell labelling for diagnostic imaging and intracavitational therapy such as radiation synovectomy and brain imaging. The lipophilicity of the metal complexes can be adjusted to optimise the desired biodistribution characteristics by suitable variation of the substituents R, $R^1$ and $R^2$.

The metal complexes of the present invention have been found to undergo more rapid hydrolysis at lower pH (e.g. pH 4–5.5) compared to neutral conditions (pH 7.0±0.5) or alkaline conditions (pH 8.0–14). NMR studies have shown that the hydrolysis results in the irreversible cleavage of the metal-coordinated C=N imine bond with concomitant release of the corresponding aldehyde or ketone. When more than one coordinated imine bond is present, the hydrolysis is believed to occur in a stepwise manner with the hydrolysis of the second and third imine bonds being more rapid than that of the first imine bond hydrolysis. The metal hydrolysis product depends on the number of imine bonds in the ligand and the nature of the metal. Where only one or two imine bonds are present, the product is expected to be the metal complex of the partly hydrolysed ligand. Lanthanide amine complexes are unstable in aqueous solution, hence for lanthanide and similar metal complexes with 3 imine bonds, the final products are likely to be free (i.e. uncomplexed) metal ion.

Selected regions of biological systems may be at lower pH. These include the lysosomes of polymorphonuclear leucocytes (PMN's) where the pH is 4.5; inflammatory synovial fluids (which are rich in lysosomal enzymes); chronic hypoxic regions (where the pH can be 0.6–0.8 units below that of normal tissues, sometimes as low as pH 5.8) or other sites of angiogenesis such as tumours, sites of inflammation or thrombi. This means that the metal complexes may be useful for the selective delivery of metal ions in biological systems to regions of lower pH. Thus the metal complex would transport the metal ion of interest to the site of lower pH, where the relatively rapid hydrolysis would result in selective trapping or release of the metal ion. The uncomplexed metal ion or much more hydrophilic metal complex resulting from the coordinated imine bond hydrolysis would be much less likely to cross cell membranes and hence become localised in the low pH region of interest. In other areas of the mammalian body (or other biological system) which are at more neutral pH (typically pH 7.0–7.4) the metal complex would remain predominantly intact and hence the metal ion would remain free to move down concentration gradients and hence undergo clearance. This selective targeting could be useful for the selective release of radiometals either for diagnostic imaging in vivo or for radiotherapy. Since the pH of the lysosomes of PMN's is known to be relatively low (approximately pH 4.5), the metal complexes of the present invention may cross PMN cell membranes and undergo relatively rapid hydrolysis in the lower pH environment of the lysosome. This could provide a method of selectively labelling PMN cells in the presence of other blood cells because other blood cells (in particular red blood cells which form the vast majority of blood cells) do not possess lysosomes. Since white blood cells are known to concentrate at sites of infection or inflammation in vivo, the labelled PMN cells could be used for the diagnostic imaging of infection or inflammation. The PMN cell labelling could be carried out on either cell preparations or whole blood samples in vitro, or the selectivity may be sufficient to permit direct cell labelling in the bloodstream in vivo following intravenous administration of the metal complex.

Preferred chelating agents for selective low pH metal delivery are the α-iminocarboxylate derivatives since the metal complexes of this ligand type exhibit a marked increase in hydrolysis rate below about pH 5. It is believed that the $pK_a$ of carboxylic acids is such that the site for initial protonation in the pH range 4 to 5 is the coordinated carboxylate substituent. This weakens the metal donor ability of the coordinated Y group with the effect that the metal-coordinated Y group is displaced by competing donor groups such as water or free pyruvic acid. Hydrolysis of the uncoordinated imine then follows. It has also been found that variation of the R group can significantly affect the hydrolysis rate (see Examples 8 and 9). The R=Me and Et derivatives are both found to give usefully slow hydrolysis rates in neutral pH conditions, but for R=Et hydrolysis proceeds slightly faster than when R=Me. The glyoxalate (R=H) derivative was found to hydrolyse in unbuffered (neutral) solution so rapidly that there was insufficient time to take an NMR spectrum, undergoing complete hydrolysis in less than 3 minutes. When R=i-Pr, there is a marked increase in hydrolysis rate, probably due to steric repulsion between the arms. This shows that by changing the R group, control over the hydrolysis rates of the metal complexes of the present invention can be achieved. Using this information it is possible to tailor the characteristics of the metal complex to the desired application.

It is envisaged that the susceptibility to hydrolysis (and possibly the rate of hydrolysis) can also be adjusted depending on how many of the groups $Y^1$, $Y^2$ and $Y^3$ are —N=CR—B(=O)OZ. The greater the number of coordinated imine bonds, the greater the anticipated ease of hydrolysis. When the lanthanide(III) [Ln(III)] complex of formula (1) undergoes complete hydrolysis, the final product is the free hydrated lanthanide metal(III) ion. At the human dosages necessary for MRI contrast agent applications, free lanthanide(III) ions may exhibit toxic effects in vivo. However, the present invention also provides ligands where only one or two of the $Y^1$, $Y^2$, $Y^3$ moieties contains an imine bond. Y groups which do not contain an imine are not expected to undergo hydrolysis, and hence such groups provide a means for residual metal chelating capacity when the Y group(s) which do contain an imine bond have been hydrolysed. Thus for example complex 5 (Scheme 5) would be expected to retain the lanthanide metal(III) ion following hydrolysis since the hydrolysed ligand is octadentate. Thus for MRI and other applications where significant human doses are involved, it is preferred that the lanthanide metal complex has only one or two imine bonds, most preferably only a single imine bond. Additionally, complex 5 has no spare coordination sites for the coordination of water molecules, and is therefore expected to give a relatively weak MRI enhancement. In a region of low pH, however, the metal complex 5 will hydrolyse giving a product with a reduced number of donor sites provided by the ligand and hence allowing the coordination of a water molecule. The product complex is thus expected to exhibit much greater MRI enhancement properties. These properties permit the possibility of selective delivery, and optionally trapping, of MRI enhancement to low pH regions within the human body.

When the metal complexes of the present invention are intended for human use, they can be administered either orally, intrathecally or (preferably) intravenously. In the special case of administration of the agents to synovial fluid, the agent may be injected directly into the synovial fluid (intra-articular injection) by a skilled physician. Such agents for human use may optionally be supplied in unit dose form in a pre-filled sterile syringe. When the metal is a radiometal, the pre-filled syringe would be fitted with a syringe shield to protect the operator from radiation dose. The metal complexes may also be supplied in kit form. The kit would preferably be sterile and contain either the ligand or reagents for the in situ preparation of the ligand ideally in freeze-dried form. The kit would give the desired metal complex on reconstitution with the metal ion of interest. The kits or pre-filled syringes may optionally contain further ingredients such as buffers; pharmaceutically acceptable solubilisers (e.g. cyclodextrins or surfactants such as Pluronic, Tween or phospholipids); pharmaceutically acceptable stabilisers or antioxidants (such as ascorbic acid, gentisic acid or para-aminobenzoic acid) or bulking agents for lyophilisation such as sodium chloride or mannitol.

The following Examples illustrate the invention. Examples 1 and 4 to 6 provide syntheses of ligands of the present invention. Example 2 provides a method of preparation of yttrium complexes with various substituents (R). Example 3 gives the synthesis of an indium complex. Example 7 provides a synthesis of an asymmetric ligand and metal complexes thereof. Examples 8 and 9 provide evidence for the differential rates of hydrolysis at different pH values, and show that the rates are essentially unaffected by the presence of liposomes. Example 10 shows that the metal complexes can penetrate liposomes (i.e. have the right properties to permit crossing biological membranes). Example 10 also shows that the amount of metal trapped within the liposome increases as the pH is lowered. Example 11 shows that the metal complexes have useful MRI relaxivity properties. The Examples show that the metal complexes of the present invention are water soluble, capable of crossing lipid membranes and release yttrium(III) much faster at the acidic pH associated with the interior of lysosomes, than at neutral pH as found in the blood and cell cytoplasm. These results demonstrate that these complexes have potential utility for the selective delivery and trapping of metal ions to areas of biological systems which are at lower pH, such as the lysosomes of cells.

EXAMPLE 1

Synthesis of tris(3-Aza4-carboxy-3-pentenyl)amine.

Sodium pyruvate was partially dissolved in MeOH at room temperature. Tris(2-aminoethyl)amine (tren, 0.33 equivalents) was added and the mixture refluxed for 2 hours, giving a pale yellow solution. The solution was allowed to cool and excess ether added giving tris(3-aza4-carboxy-3-pentenyl)amine as a white precipitate.

$^1$H NMR (d$_4$-MeOH): δ 3.48 (t,2H), 2.82 and 2.76 (both t,2H), 2.08 and 2.04 (both s, 3H) ppm (mixture of cis and trans isomers).

EXAMPLE 2

Synthesis of the Lanthanide (Ln) Complexes of tris(3-Aza-4-carboxy-3-pentenyl)amine and Analogues.

Method A.

Sodium pyruvate (330 mg, 3 mmol) was partially dissolved in MeOH (40 cm$^3$) at room temperature. The solution was stirred, and 1 mmol of the appropriate metal(III) chloride added followed by slow addition (over 1 minute) of tris(2-aminoethyl)amine (tren, 146 mg, 1 mmol). During addition of the tren, a white precipitate of Ln(OH)$_3$ sometimes formed but this always quickly re-dissolved. The resultant clear, colourless solution was then heated to reflux for 2 h. The solution was then allowed to cool and excess Et$_2$O (250 cm$^3$) was added to yield a white precipitate, this was filtered off under gravity. The precipitate was washed with further Et$_2$O (100 cm$^3$) as it was being filtered to remove traces of MeOH. The resulting white solid was dried in vacuo. Removal of impurity NaCl was achieved by elution of a concentrated solution of this product in MeOH through a Sephadex LH-20 column made up in a micropipette, and allowing the solution to pass through under gravity. Yield of complex—NaCl mixtures was as follows:

| metal: | Y | Yb | Gd | Sm | Pr | Lu | La | Sr |
|---|---|---|---|---|---|---|---|---|
| yield (%) | 87–99 | 97 | 95 | 92 | 91 | 96 | 87–91 | 32 |

Y(III) complex: $^1$H NMR (D$_2$O, unbuffered) δ=3.19(t, 2H), 3.80(t, 2H), 2.05(s, 3H); electrospray mass spectrum (H$_2$O) m/z 1769=[{Y(L$^1$)}$_4$+H]$^+$, 1327=[{Y(L$^1$)}$_3$+H]$^+$, 885=[{Y(L$^1$)}$_2$+H]$^+$, 443=[Y(L$^1$)+H]$^+$; IR (KBr disk) 1625vs, 1368s(br), 1202s.

The corresponding Y(III) complexes of the ligands corresponding to the R=H, Et, i-Pr and Ph analogues (see Scheme 1) were synthesised using the same method using the appropriate a-ketone carboxylate sodium salt. $^1$H NMR data for the Y(III) complex of the ligand specified in D$_2$O is given below:

R=Et, tris(3-aza-4-carboxy-3-hexenyl)amine: (pH=7.0 buffered), δ=3.61(t, 2H), 2.96(t, 2H), 2.30 (q, 2H), 0.76 (t, 3H) ppm.

R=i-Pr, of tris(3-aza-4-carboxy-5-methyl-3-hexenyl) amine: (pH=7.0 buffered), δ=3.64 (t, 2H), 2.97 (t, 2H), 2.84 (septet, 1H), 0.99 (d, 6H) ppm.

R=Ph, tris(3-aza-4-carboxy-4-phenyl-3-butenyl)amine: (unbuffered), δ=7.46 (m, 3H), 7.27 (m, 2H), 3.78 (br s, 2H), 2.99 (br s, 3H) ppm.

Method B

Figure 2:
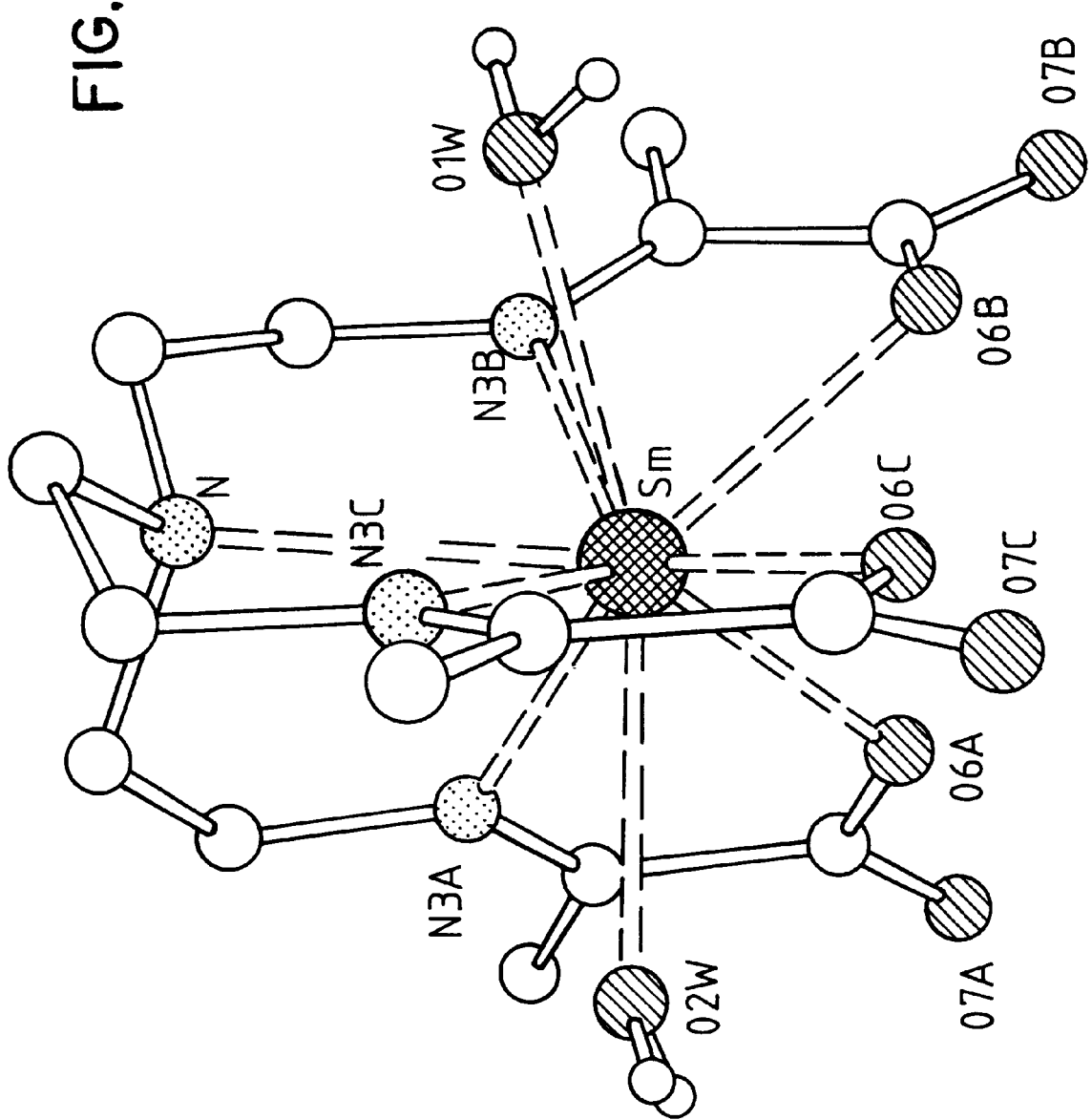
FIG. 2 shows the X-ray crystal structure of the samarium complex of tris(3-aza4-carboxy-3-pentenyl)amine.

The isolated ligand from Example 1 was reacted with the metals of Example 2 in methanol giving almost quantitative yields of the metal complex as described in Method A above. The X-ray crystal structure of the Sm(III) complex is shown in FIG. 2.

EXAMPLE 3

Preparation of the Indium Complex of (2-aminoethyl)bis(3-aza-4-carboxy-3-pentenyl)amine The method of Example 2 was followed using InCl$_3$, tren and sodium pyruvate.

Figure 1:
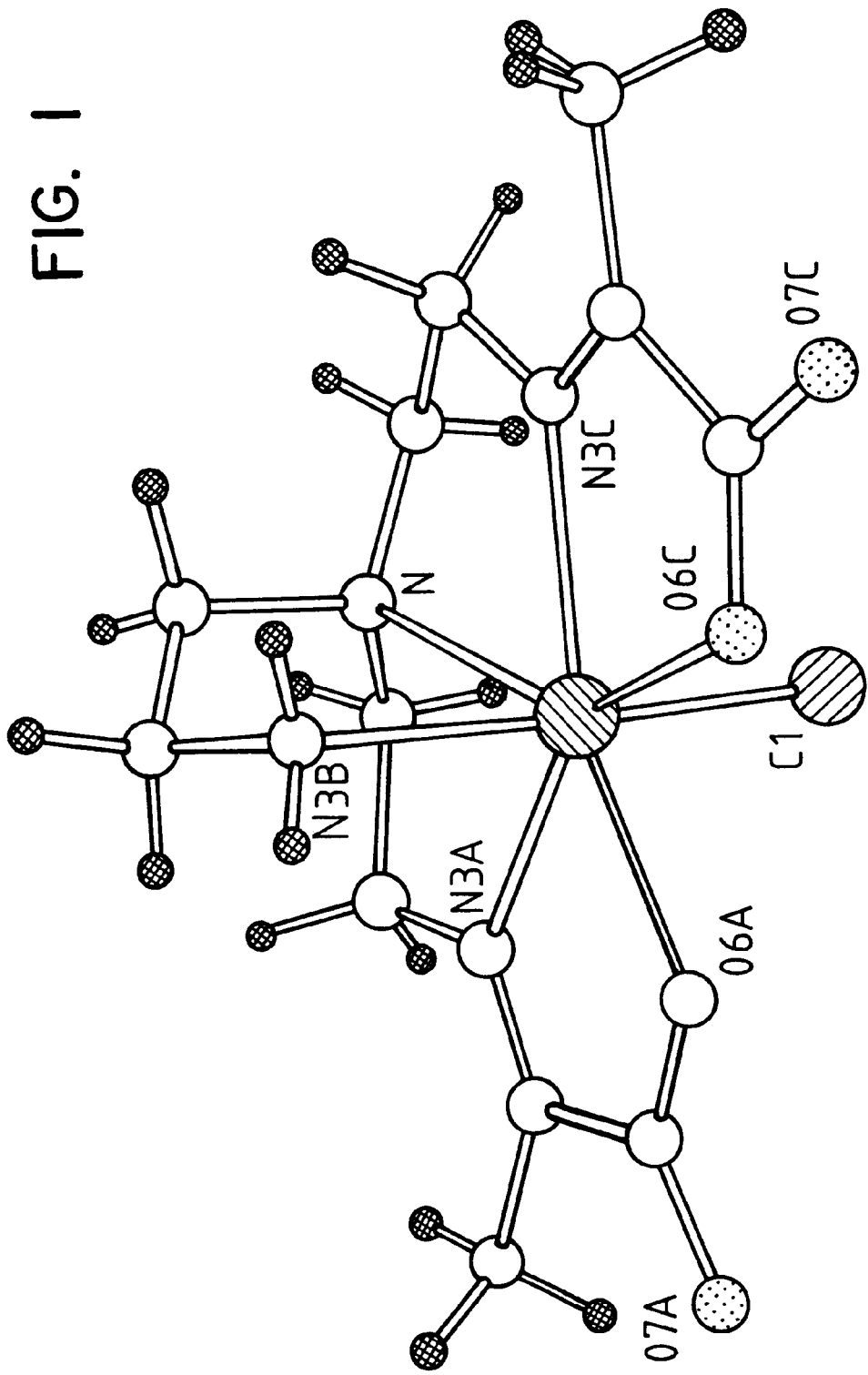
FIG. 1 shows the X-ray crystal structure of the indium complex of (2-aminoethyl)bis(3-aza-4-carboxy-3-pentenyl) amine.

The indium(III) metal complex crystallised out without the addition of Et$_2$O, yield 72%. The X-ray crystal structure of the In(III) complex shows that only two of the three tren arms had undergone Schiff-base condensation (see FIG. 1).

$^1$H NMR (D$_2$O, unbuffered): δ=3.79(m, 2H), 3.24(m, 2H), 2.88(m, 1H), 2.81(m, 1H), 2.28(s, 3H); IR (KBr disc) 1637vs, 1361s, 1200s.

EXAMPLE 4

Synthesis of tris(2-aminopropyl)amine [C$_3$-tren].

This is a new synthesis of this tripodal amine (see Scheme 2).

(i) Synthesis of tris(2-cyanoethyl)amine.

Acrylonitrile (110 g, 2 mol) was added dropwise to a stirred solution of 28% ammonia in H$_2$O (61 g, 1 mol) at 30° C. at such a rate that little or no second phase was present at any one time. Stirring was continued for 2 h at 30° C. and then water (350 cm$^3$) and more acrylonitrile (110 g, 2 mol) were added. The mixture was stirred at 75° C. for 52 h. Then water and excess acrylonitrile was removed under reduced pressure. The residual liquid crystallised on standing. Recrystallisation from hot EtOH gave clear, colourless needles. Yield: 73%.

$^{13}$C NMR (D$_2$O) δ=121.14(—CN), 48.80(CH$_2$—CN), 16.71 (N—CH$_2$—)ppm.

(ii) Synthesis of tris(2-aminopropyl)amine.

Tris(2-cyanoethyl)amine (2.80 g, 15.9 mmol) was dissolved in BH$_3$.THF and refluxed under nitrogen for 48 h. MeOH (ca. 20 cm$^3$) was added dropwise to the solution with vigorous stirring until no more gas was evolved. The solution was evaporated to dryness under vacuum and the resultant white precipitate refluxed in 6M hydrochloric acid (250 cm$^3$) until the solution cleared. The hydrochloric acid was removed under reduced pressure and the resultant solid was dissolved in the minimum amount of water. The solution was divided up into two portions. Each portion was applied to a basic ion exchange column (DOWEX ion exchange resin, 20–50 mesh) and the amine eluted in water (ca. 250 cm$^3$). The water was removed under reduced pressure to yield Tris(3-aminopropyl)amine (1.78 g, 59%) as a clear oil.

$^1$H NMR: (CDCl$_3$) δ=2.71 (6H, t, N(CH$_2$CH$_2$CH$_2$NH$_2$)$_3$, 2.44 (6H, t, N(CH$_2$CH$_2$CH$_2$NH$_2$)$_3$, 1.57 (6H, q, N(CH$_2$CH$_2$CH$_2$NH$_2$)$_3$, 1.36 (6H, br, N(CH$_2$CH$_2$CH$_2$NH$_2$)$_3$.

EXAMPLE 5

Synthesis of Phosphorus-containing Ligands.

When B is P, the ligands may be prepared via an acylphosphonate salt (see Scheme 1). The required acylphosphonate may be prepared by the method of Karaman et al [R. Karaman, A. Goldblum, E. Breuer, H. Leader, *J. Chem. Soc. Perkin Trans.* 1, 1989, 765–774]. Thus, reaction of trimethyl phosphite with a suitably chosen acid chloride RCOCl at 5° C., gives the dimethyl acylphosphonate in high yield. Reaction of the dimethyl acylphosphonate with sodium iodide in dry acetone (or LiBr in dry MeCN) gives the methyl acylphosphonate mono salt in high yield. The metal tri-imino-tri-phosphonate complex is then formed by reacting three equivalents of methyl acylphosphonate mono salt with one equivalent of tris(2-aminoethyl)amine and one equivalent of the chosen metal salt in methanol under reflux for 2 h. The product can then be precipitated upon the addition of ether, and purified by elution through a Sephadex LH-20 column.

EXAMPLE 6

Synthesis of Macrocyclic Iminocarboxylate Complexes Based upon [9]aneN$_3$ (See Scheme 4).

(i) Synthesis of 1,4,7-tris(cyanomethyl)-1,4,7-triazacyclononane

[9]aneN$_3$.3HBr (3.0 g, 8.07 mmol), chloroacetonitrile (1.9 g, 25.2 mmol), and triethylamine (10 g, 0.099 mol) in 150 cm$^3$ of ethanol were refluxed under nitrogen for 24 h. After cooling, the solvent was removed by rotary evaporation to yield a red oil which was dissolved in CHCl$_3$ (100 cm$^3$) and washed with water (3×100 cm$^3$). The organic phase was collected and dried with MgSO$_4$, filtered and dried by rotary evaporation. The resulting yellow oil was dried in vacuo to yield a pale yellow solid. (1.052 g, 4.27 mmol) Yield: 53%.
$^1$H NMR: (CDCl$_3$) δ=2.855 (12 H, s, —NCH$_2$—), 3.594 (6 H, s, NCH$_2$CN) ppm.
$^{13}$C NMR: (CDCl$_3$) δ=54.12 (NCH$_2$), 46.49 ( NCH$_2$CN), 116.14 (CN) ppm.

(ii) Synthesis of 1,4,7-tris(aminoethyl)-1,4,7-triazacyclononane 1,4,7-tris(cyanomethyl)-1,4,7-triazacyclononane (0.320 g, 1.23 mmol) and BH$_3$.THF 1 M solution in THF (40 cm$^3$) were refluxed under nitrogen for 48 h. After cooling, excess borane was destroyed by adding water (5 cm$^3$), then the solution was dried under vacuum. The white solid obtained was dissolved in 50 cm$^3$ of HCl 7M and heated under reflux for 40 h. After cooling, the solution was dried in vacuum to yield a white solid. The solid was dissolved in the minimum amount of water and the solution obtained was passed through a Dowex 1×8–200 column (10 g) activated with a solution 1M of sodium hydroxide. The solvent was removed under reduced pressure to yield a colourless oil. (0.270 g, 1.045 mmol) Yield: 85%.
$^1$H NMR: (CDCl$_3$) δ=2.76 (12 H, s, NCH$_2$), 2.75, 2.59 (12 H, dt, CH$_2$CH$_2$N), 1.63 (6 H, broad, NH$_2$) ppm. $^{13}$C NMR: (CDCl$_3$) δ=56.90 (NCH$_2$), 62.21 (NCH$_2$CH$_2$NH$_2$), 40.26 (NCH$_2$CH$_2$NH$_2$) ppm.

(iii) Synthesis of the Ln(III) complexes [Ln(L)] (Ln=Y, Sm, La, Yb).

The synthesis of the Y(III) complex is typical:
1,4,7-tris(aminoethyl)-1,4,7-triazacyclononane (39.8 mg, 0.154 mmol), sodium pyruvate (50.9 mg, 0.462 mmol) and yttrium nitrate (56.2 mg, 0.154 mmol) were heated to reflux in methanol (30 cm$^3$) for two hours. After cooling, the solvent volume was reduced and diethyl ether was added: a pale yellow solid was obtained. The solid was filtered off and dried under vacuum. The sodium nitrate was removed from the yttrium complex by passing a concentrated methanolic solution of the solid through a LH-20 Sephadex column. Addition of diethyl ether yielded a white solid. (61.2 mg, 0.11 mmol) Yield: 71.4%. A single crystal suitable for X-ray analysis was obtained by diffusion of diethyl ether vapour into a methanol solution of the complex at room temperature.
Mass spec. (Electrospray) m/z=577 (M$^+$[C$_{21}$H$_{33}$N$_6$O$_6$Y+Na$^+$]).
$^{13}$C NMR: (CD$_3$OD) δ=53.72 (NCH$_2$), 60.31 (NCH$_2$CH$_2$N), 60.17 (NCH$_2$CH$_2$N), 172.68 (N=C), 17.15 (CH$_3$), 173.76 (CO$_2$) ppm.

Figure 3:
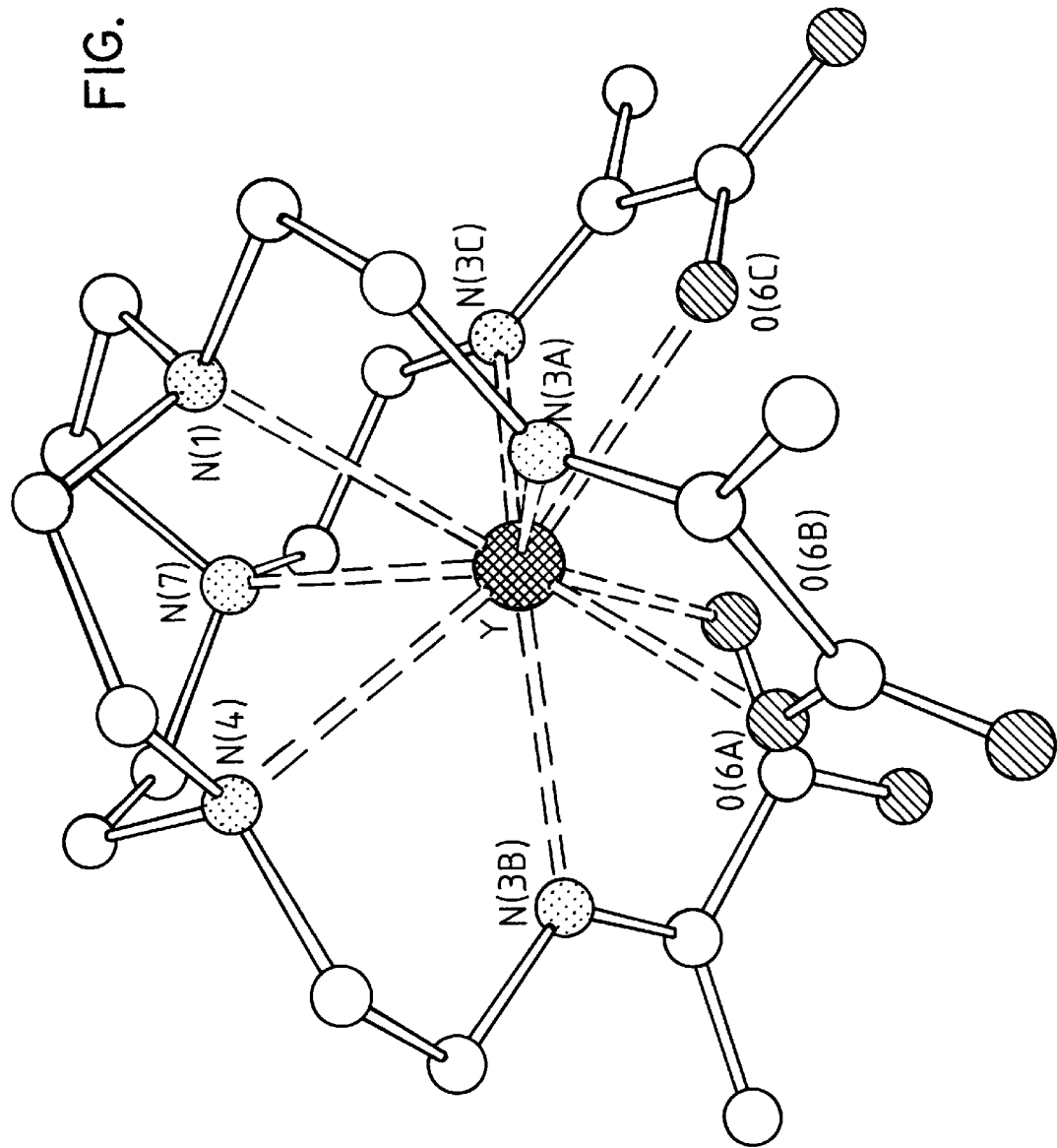
FIG. 3 shows the X-ray crystal structure of the yttrium complex of a ligand where A is 1,4,7-triazacyclononane.

This procedure was successfully completed for complexes of Ln=Y, Sm, La, Yb, all of which have been characterised by single crystal X-ray diffraction. These structures show all the complexes to be isostructural with observed 9-co-ordination at the Ln centres (FIG. 3). Other lanthanide metal ions can be expected to bind to these macrocyclic iminocarboxylate ligands in a similar manner.

EXAMPLE 7

Synthesis and Application of an Asymmetric Complex.

Scheme 5 illustrates how such asymmetric tripodal ligands can be synthesised.

(i) Synthesis of 1

BOC—ON (4.92 g, 20 mmol) was dissolved in dry THF (50 cm$^3$). This solution was added dropwise over 30 min to a rapidly stirred solution of tris(2-aminoethyl)amine (2.92 g, 20 mmol) in dry THF (300 cm$^3$) 0° C. The resulting reaction mixture was stirred at 273K for 4 h. The solvent was removed under reduced pressure leaving a thick yellow oil. This oil was redissolved in boiling ether, and left to cool for 10 h, and a second yellow oil separated out which was discarded. The solvent was removed from the supernatant solution under reduced pressure to yield a third yellow oil of impure 1. Yield: 67%.
$^1$H NMR: (CDCl$_3$) δ=7.75 and 7.40 (m, aromatic impurity derived from BOC—ON), 5.20 (1H,br, NHBOC), 4.55 (2H,br,NH$_2$), 3.19 (2H,m,CH$_2$NHBOC), 2.81 (4H,t,C H$_2$NH$_2$), 2.59 (6H,m,NCH$_2$CH$_2$) 1.44 (9H,d,CH$_3$ on BOC group) ppm.

The doubly-protected derivative, N(CH$_2$CH$_2$NH$_2$)(CH$_2$CH$_2$NHBOC)$_2$ can be synthesised using the same method but using 2 equivalents of BOC—ON.

(ii) Synthesis of 4

Tris(2-aminoethyl)amine (1.02 g, 7.0 mmol) was added to a solution of 2-bromoethyl acetate (7.01 g, 42 mmol) in CHCl$_3$ (50 cm$^3$). The resulting mixture was stirred at room temperature for 2 h to give a white precipitate. The reaction mixture was filtered. $^1$H NMR analysis revealed that the white precipitate was a bromide salt of protonated tren. The solvent was removed from the filtrate under reduced pressure to yield a brown oil. Unreacted 2-bromoethylacetate was removed by distillation at 60° C. in vacuo, leaving a residual thick brown oil 4. Yield: 41%
$^1$H NMR: (CDCl$_3$) δ=4.14 (4H,q,—OCH$_2$CH$_3$), 3.78 (2H, t,NCH$_2$CH$_2$), 3.58 (4H,s,—CH$_2$COO—), 3.27 (2H,t,NC H$_2$CH$_2$), 1.24 (6H,t,—OCH$_2$CH$_3$).

(iii) Synthesis of 2 and 3

The method for the synthesis of 4 as described above can also be suitably adapted for use in the synthesis of 2. Ligand 2 may be deprotected by stirring in a MeOH/6M HCl in H$_2$O mixture for 36 h. The solvent is then removed under reduced pressure. The resulting compound is then dissolved in MeOH and 1 equivalent of LnCl$_3$.6(H$_2$O) and 1 equivalent of the Na$^+$-salt of an 2-keto carboxylic acid added. Then, NaOH in MeOH is added to the solution until just alkaline, and the resulting solution refluxed for 2 h. Addition of excess ether would precipitate complex 3.

EXAMPLE 8

Hydrolysis Rate Studies.

A 20 mg sample of the Y(III), R=Me complex of Example 2 was dissolved in D$_2$O containing an imidazole buffer (pH=7.0), and left to stand at room temperature. The $^1$H NMR spectrum of the solution was measured at timed intervals (t, in hours) over a period of two days (see Scheme 6). During this time the triplet peaks at 2.91 ppm (A) and 3.51 ppm (B) decreased in intensity and two new peaks appeared at 2.63 ppm (C) and 2.92 ppm (D), consistent with the hydrolysis of the complex occurring to yield protonated tren. By taking the relative integrals of these peaks, it was possible to monitor the dissociation as a function of time. This experiment was repeated with an acetic acid/potassium acetate buffer (pH=4.7).

| | [Complex]$_t$/[Complex]$_{t=0}$ | |
|---|---|---|
| Time/h | pH = 7.0 | pH = 4.7 |
| 0.0 | 1.00 | 1.00 |
| 1.2 | 0.85 | 0.33 |
| 6.1 | 0.65 | 0.02 |
| 9.9 | 0.47 | |
| 21.0 | 0.19 | |

The data shows that decomposition of the ligand and subsequent release of the yttrium ions occurs fastest at low pH values, when total hydrolysis of the sample is complete in a few hours. At neutral pH the complex is much longer lived, with the decomposition still not complete after 21 h. Hydrolysis of the complex at approximately the same rates as these have been observed in the presence of liposomes.

The experiment was repeated with R=Et or i-Pr as alternatives to R=Me, with the following results.

| | [Complex]$_t$/[Complex]$_{t=0}$ | | |
|---|---|---|---|
| Time/h | R = Me | R = Et | R = i-Pr |
| 0 | 1.00 | 1.00 | 1.00 |
| 1.0 | 0.83 | 0.79 | 0.26 |
| 3.8 | 0.70 | 0.63 | 0.0 |
| 10.0 | 0.45 | 0.37 | |
| 22.1 | 0.16 | 0.13 | |

EXAMPLE 9

Hydrolysis of the Y(III) complex of tris(3-aza-4-carboxy-4-phenyl-3-butenyl)amine (formula (1) with R=Ph)

Y(III) (R=Ph) complex/NaCl (7 mg) was dissolved in $d_4$-MeOH (0.1 cm$^3$). An equimolar amount of Y(III) (R=Me) complex/NaCl was also dissolved in an $d_4$-MeOH (0.1 cm$^3$). Both samples were then transferred to NMR tubes and D$_2$O (0.48 cm$^3$) containing an imidazole pH=7.0 buffer was added to each samples at the same time. The NMR spectra of both samples were then taken at timed intervals over a 2 day period to monitor the hydrolysis of the complexes. The temperature of the two samples was maintained at 293K throughout the 2 day period. The results are summarised table below:

| | [Complex]$_t$/[Complex]$_{t=0}$ | |
|---|---|---|
| Time/h | [R = Ph] | [R = Me] |
| 0 | 1.00 | 1.00 |
| 2.0 | 0.56 | 0.81 |
| 5.8 | 0.41 | 0.72 |
| 10.9 | 0.31 | 0.67 |
| 25.5 | 0.15 | 0.48 |
| 52.3 | 0.05 | 0.24 |

It can be seen that there is fast hydrolysis of the R=Ph derivative compared to the R=Me derivative. This may be attributed to the additional steric crowding between the tripod arms when R=Ph.

The small amount of $d_4$-MeOH aids dissolution of [R=Ph].3NaCl in D$_2$O, and does not significantly change the hydrolysis rate. Unfortunately, it was still not possible to dissolve a larger quantity of [R=Ph].3NaCl which would allow direct comparison with the data already obtained for the R=Me, Et and i-Pr derivatives. However, by comparison with the R=Me derivative, it appears that the hydrolysis rate of the R=Ph derivative lies between the rates of the R=Et and i-Pr derivatives. Therefore, the relative hydrolysis rates are:

H>>i-Pr>Ph>Et>Me.

EXAMPLE 10

Lipid Membrane Permeability Studies.

(a) Manufacture of Liposomes.

A 1 cm$^3$ sample of liposomes was prepared by the method of Fry et al [D. W. Fry, C. White, D. J. Goldman, Anal. Biochem., 90, 809(1978)].

Thus, dipalmitoylphosphatidyl choline C16:0 (13 mg), cholesterol (1 mg) and stearylamine (1 mg) were placed in a glass vial. Two glass beads were added, and the vial sealed (with a rubber septum and crimped on metal overseal). The mixture was vigorously stirred to give a clear, colourless solution. This solution was evaporated to dryness at 60° C. under a stream of nitrogen gas, to give a white solid (lipids) on the side of the vial, which could be stored at −20° C. in the sealed vial until use.

(b) Liposome permeability studies by ICP.

50 mg of the Y(III), R=Me complex/NaCl mixture were dissolved in 1 cm$^3$ of degassed water containing an imidazole buffer (pH=7.04). This was added to a vial of solid lipids (prepared as described above). The mixture was vigorously stirred until the lipids no longer adhered to the sides of the vial, then sonicated for 5 min during which time the lipids formed into spherical liposomes of constant size (as seen under a microscope), encasing some of the complex. The vial was then allowed to stand for exactly 3 h at room temperature, to allow some of the complex to hydrolyse. Four 1 cm$^3$ syringe barrels were plugged with glass wool and filled with Sephadex G50 in 0.9% saline. These syringe barrels were suspended in test tubes and centrifuged at 2000 rpm for 2 min, after which time the top of the Sephadex had dropped to the 0.9 cm$^3$ graduation, and had come away from the sides of the syringe barrel. The columns were then each washed through with 0.3 cm$^3$ of the degassed imidazole buffer solution, and centrifuged again for 2 min at 2000 rpm. 0.25 cm$^3$ of the liposomes were then added to each column and centrifuged for 2 min at 2000 rpm. This had the effect of removing the supernatant complex, whereas the liposomal complex passed through the column, within the liposomes. The liposomes were then left to stand for 110 min at room temperature, to allow internal complex to diffuse out. After this time, the liposomes were passed through another Sephadex column as before, to remove the supernatant complex. Then, 0.05 cm$^3$ of Triton X-100 was added to the liposomes, and the sample left to stand for several hours until the solution was clear and the liposomes had been broken down. The solution was made up to 100 cm$^3$ in 10% HNO$_3$ and analysed for yttrium by ICP. This experiment was repeated with acetate pH=4.93 and pH=3.91 buffers, and also a control in which the complex had been left to stand overnight in the pH=3.91 buffer to allow total hydrolysis.

| pH | Yttrium detected in liposomes/ppm |
|---|---|
| 7.04 (imidazole) | 0.95 |
| 4.93 (acetate) | 1.67 |
| 3.91 (acetate) | 1.91 |
| 3.91 (acetate, control) | 4.93 |

In the neutral pH case, the yttrium can be expected to be largely in the complexed form after 3 h hydrolysis, whereas at acidic pH values, the complex will have largely hydrolysed after this time and the yttrium will free. In the case of the control, all of the complex will have hydrolysed leaving 100% free trivalent yttrium cations. These results show that the neutral complexed yttrium readily diffuses out of the liposomes, but free, charged yttrium remains trapped inside.

A variation of this experiment was completed in which 5 cm$^3$ of liposomes were made up in which 250 mg of complex in imidazole pH=7.04 buffer were left to hydrolyse for only 10 min. The supernatant complex was removed as before, and the complex allowed to diffuse out of the liposomes. At certain timed intervals, a 1 cm$^3$ portion of this was taken, the supernatant yttrium removed, and the liposomes analysed for yttrium by ICP as before.

| Time/h | pH = 7.04 Yttrium detected in liposomes/ppm |
|---|---|
| 0.3 | 1.03 |
| 0.8 | 1.14 |
| 1.8(frompHexpt) | 0.95 |
| 2.3 | 0.98 |
| 19.0 | 1.12 |

The yttrium detected is very similar in all cases, within experimental error, and consistent with that detected in the previous pH experiments. This indicates that diffusion of the complex out of the liposomes is very rapid with an equilibrium being reached within 20 min.

(c) Lipid permeability study by NMR 100 mg of the R=Me yttrium complex/NaCl mixture were dissolved in D$_2$O containing an imidazole buffer (pH=6.80). This was incorporated inside the liposomes as described in Example 5(b) above. The complex was given an initial hydrolysis time of under 10 min, then a further 90 min while the complex was allowed to diffuse out of the liposomes. In order to obtain an NMR spectrum of sufficient clarity, it was necessary to look at the supernatant fraction, rather than the liposome fraction. The liposomes were passed through the Sephadex G50 as before, but then discarded. Any supernatant complex was then trapped in the Sephadex. The Sephadex was washed through once with 0.2 cm$^3$ deuterated buffer solution in each syringe, then centrifuged at 2000 rpm for 2 min, then this fraction was also discarded. Then a further 0.3 cm$^3$ of deuterated buffer was washed through (2 min spin, 2000 rpm), this fraction was collected (a clear, colourless liquid) and analysed by $^1$H NMR.

The NMR showed only imidazole, water, ethanol (from liposome manufacture) and the complex peaks [d=3.65 (t, 2H), 3.02 (t, 2H), 1.97 (s,3H)]. This provides further proof that the complex is able to pass through lipid membranes intact.

EXAMPLE 11

Relaxivity of the GD(III) complex of tris(3-aza-4-carboxy-3-pentenyl)amine, (formula (1) with R=H), hereafter [Gd(L)]

A sample of [Gd(L)].3NaCl was weighed and dissolved in 0.10 cm$^3$ of d$_4$-MeOH, a solvent in which [Gd(L$^1$)] does not hydrolyse. A further five samples each containing a different mass of [Gd(L)].3NaCl were made up in the same way. The first sample was transferred to an NMR tube and mixed with 0.48 cm$^3$ of D$_2$O. The transverse relaxation time (T$_1$) of the HOD peak at 4.707 ppm was measured using a 180-J-90 pulse sequence at 37° C. using a Bruker 300 MHz NMR spectrometer. This was repeated for the remaining five samples. In all cases, the delay between adding D$_2$O and completing the T$_1$ measurement was less than 30 minutes, a time interval over which hydrolysis of the complexes is minimal. A final sample was made up in the same way using pure [Gd(L)] (made by eluting [Gd(L)].3NaCl through a Sephadex LH-20 column). The results are summarised below:

| Mass [Gd(L)].3NaCl/g | Concentration of [Gd(L)]/mM$^{-1}$ | T$_1$/s | 1/T$_1$/s$^{-1}$ |
|---|---|---|---|
| 0.0014 | 3.53 | 0.1002 | 9.98 |
| 0.0020 | 5.04 | 0.0472 | 21.18 |
| 0.0026 | 6.56 | 0.0332 | 30.09 |
| 0.0032 | 8.07 | 0.0279 | 35.77 |
| 0.0038 | 9.58 | 0.0230 | 43.57 |
| 0.0060 | 15.13 | 0.0156 | 64.02 |
| 0.0034(mass[Gd(L)]) | 11.51 | 0.0217 | 46.17 |

Plotting 1/T$_1$ against concentration results in an approximate straight line. The relaxivity of [Gd(L)] is calculated by taking the gradient of this graph. Thus the relaxivity of [Gd(L)] at 37° C. and 300 MHz is (4.3±0.6) s$^{-1}$mM$^{-1}$.

We have previously prepared a range of adducts [Ln(L)]/NaCl. Passing these through a Sephadex column results in crystallisation of the Na$^+$-free species [Ln(L)], the single crystal X-ray structures of which show [for Ln=Y(IIII), Yb(III)] the formation of polynuclear aggregates in the absence of H$_2$O. If these aggregates existed in H$_2$O solution they would be expected to show lower relaxivity than a monomer with 1 or 2 co-ordination sites occupied by H$_2$O molecules. However, the 1/T$_1$ graph shows that the point corresponding to pure [Gd(L)] lies very close to the line of [Gd(L)].3NaCl. This implies that in H$_2$O all of these complexes, and particularly [Gd(L)] and [Gd(L)].3NaCl, dissolve to give the same species with the same number of coordinated H$_2$O molecules. We have confirmed that two H$_2$O molecules bind to these complexes since single crystal X-ray structures of [Ln(L)] recrystallised from H$_2$O show nine-co-ordinate structures of type [Ln(L)(OH$_2$)$_2$] (Ln=Gd, Sm). These structural studies are summarised in our publication *J. Chem. Soc., Dalton Trans.*, 1997, 3655.

| Agent | Relaxivity/s$^{-1}$mM$^{-1}$ | Field/MHz | Temp/° C. |
|---|---|---|---|
| [Gd(L)] | 4.3 | 300 | 37 |
| Magnevist or [Gd(DTPA)]$^{2-}$ | 3.7 | 20 | 37 |
| Gadodiamide | 4.6 | 10 | 37 |
| [Gd(DOTA)]$^-$ | 3.4 | 20 | 37 |

The relaxivity of [Gd(L)] at 300 MHz cannot be accurately compared with the relaxivity values of other MRI agents which are usually measured at 10 or 20 MHz. However, since relaxivity usually decreases with increased magnetic field strength[1], the relaxivity of [Gd(L)] is greater than DTPA- and DOTA-based MRI agents. This can be attributed to the greater number of co-ordinated H$_2$O molecules bound to [Gd(L)] compared to [Gd(DTPA)]$^{2-}$ and [Gd(DOTA)]$^-$.
[1] S. Aime, A. S. Batsanov, M. Botta, J. A. K. Howard, D. Parker, K. Senanayake, G. Williams, *Inorg. Chem.*, 1994, 33, 4696–4706.
Scheme 1
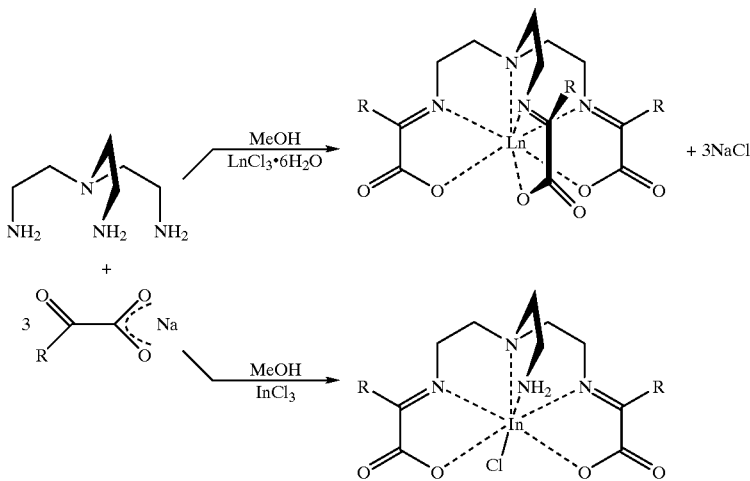
Scheme 6
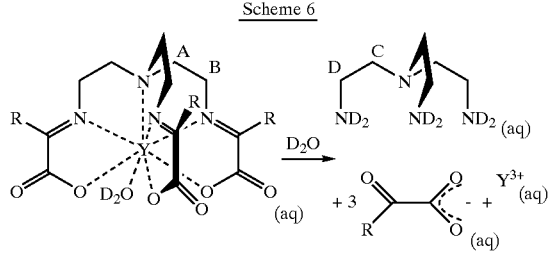
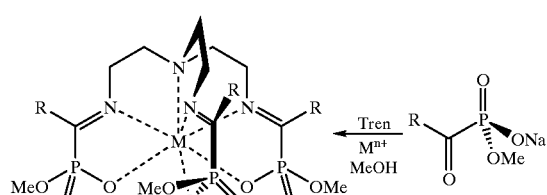
Scheme 2
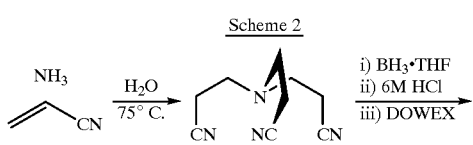
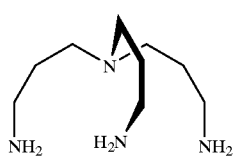
Scheme 4
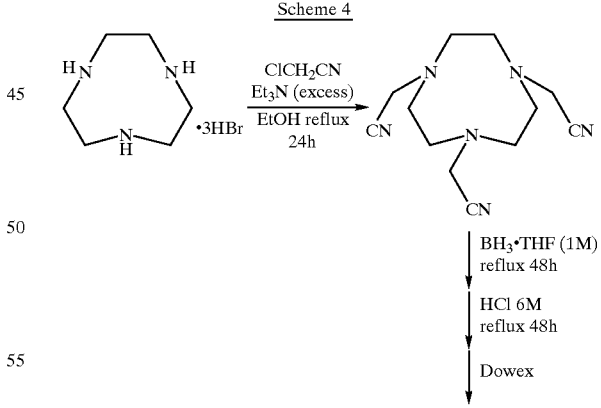
Scheme 3
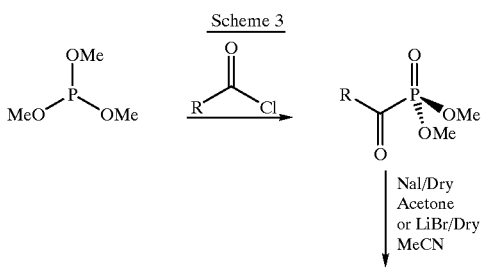
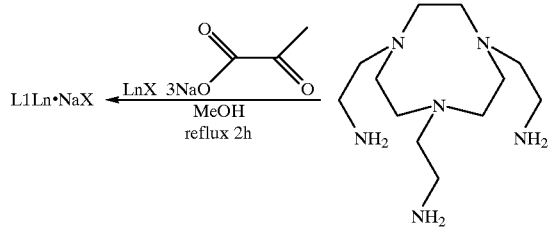

Scheme 5

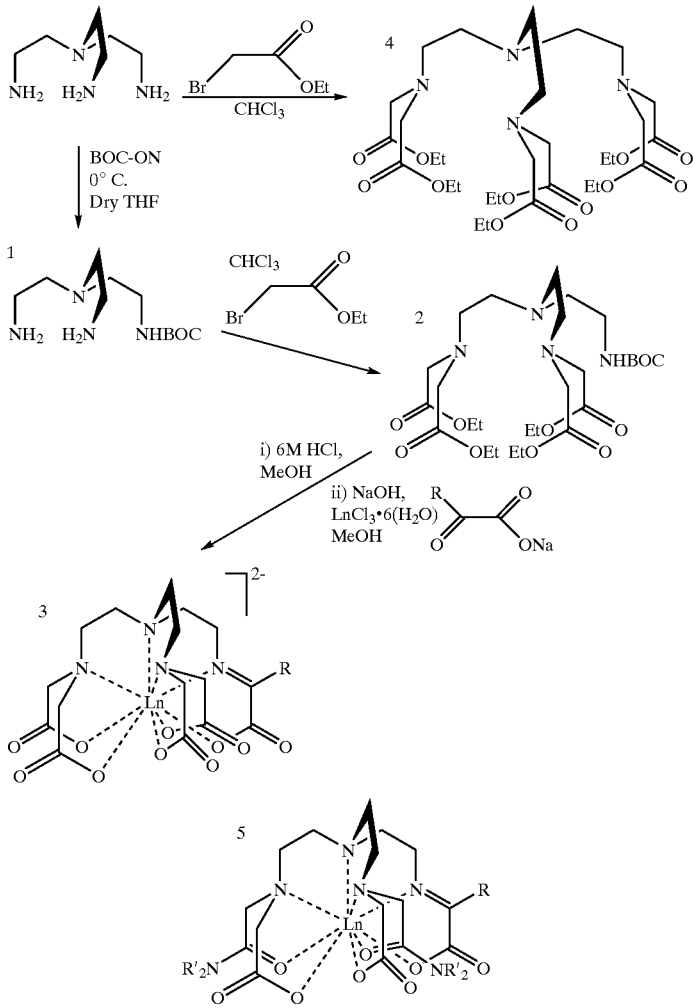

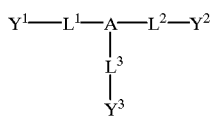

Ln = Y, La, Sm
X = NO$_3$, CF$_3$COO, Cl

What is claimed is:

1. A ligand of formula:

$$Y^1-L^1-A-L^2-Y^2$$
$$|$$
$$L^3$$
$$|$$
$$Y^3$$

where:

A is N, CR$^1$, P, P=O, cis,cis,cis-1,3,5-trisubstituted-cyclohexane or an N,N',N''-trisubstituted-triaza 9 to 14 membered macrocyclic ring;

L$^1$, L$^2$, L$^3$ are linker groups which are independently chosen from C$_{1-4}$ alkylene, C$_{4-6}$ cycloalkylene or C$_{4-6}$ o-arylene;

Y$^1$, Y$^2$, Y$_3$ are independently chosen from —NH$_2$, —B(=O)OZ, —N=CR—B(=O)OZ, —NR—CR$_2$—B(=O)OZ, —N[CR$_2$—B(=O)Q]$_2$ and —O—CR$_2$—B(=O)OZ where B is C or PR$^2$, each Q is independently —OZ or —NR$_2$ and Z is H or a counter-ion;

each R and R$^1$ group is independently chosen from H, C$_{1-5}$ alkyl, C$_{1-5}$ alkoxyalkyl, C$_{1-5}$ hydroxyalkyl, C$_{1-5}$ aminoalkyl, C$_{5-10}$ aryl or C$_{1-8}$ fluoroalkyl;

R$^2$ is OH, C$_{1-6}$ alkyl, C$_{1-8}$ alkoxyalkyl, C$_{1-6}$ fluoroalkyl, C$_{1-10}$ alkoxy or C$_{5-10}$ aryl;

with the proviso that at least one of Y$^1$, Y$^2$ and Y$^3$ is —N=CR—B(=O)OZ.

2. The ligand of claim 1 where A is N or CR$^1$, L$^1$, L$^2$ and L$^3$ are all the same and are C$_{1-3}$ alkylene and Y$^1$, Y$^2$ and Y$^3$ are all —N=CR—B(=O)OZ.

3. The ligand of claim 2 where A is N, L$^1$, L$^2$ and L$^3$ are all —CH$_2$CH$_2$— and B is C.

4. A metal complex of the ligand of claim 1.

5. The metal complex of claim 4 where the metal complex is neutral.

6. A metal complex of the ligand of claim 3 of formula (1):

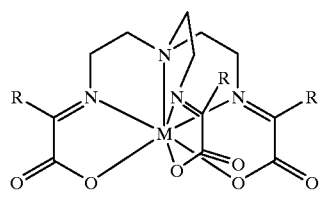

where M is the metal.

7. The metal complex of any one of claim 4 where the metal is a lanthanide metal, indium or gallium.

8. The metal complex of claim 4 where the metal is radioactive.

9. The metal complex of claim 8 where the metal is $^{90}$Y, $^{153}$Sm, $^{111}$In or $^{169}$Yb.

10. The metal complex of claim 4 where the metal is paramagnetic.

11. The metal complex of claim 10 where the metal is gadolinium.

* * * * *

UNITED STATES PATENT AND TRADEMARK OFFICE
CERTIFICATE OF CORRECTION

PATENT NO. : 6,153,775
DATED : November 28, 2000
INVENTOR(S) : Schroder et al.

It is certified that error appears in the above-identified patent and that said Letters Patent is hereby corrected as shown below:

Column 17,
Line 65, "$Y_3$" should be -- $Y^3$ --.

Column 18,
Line 54, "$C_{1-8}$ alkoxyalkyl" should be -- $C_{1-6}$ alkoxyalkyl --.

Signed and Sealed this

Twenty-eighth Day of August, 2001

Attest:

*Nicholas P. Godici*

NICHOLAS P. GODICI
*Attesting Officer*    *Acting Director of the United States Patent and Trademark Office*